(12) United States Patent
Bhalla et al.

(10) Patent No.: US 11,103,604 B2
(45) Date of Patent: *Aug. 31, 2021

(54) METAL COMPLEXES AND FLUORINATION THEREOF

(71) Applicants: GE Healthcare Limited, Buckinghamshire (GB); University of Southampton, Southampton (GB)

(72) Inventors: Rajiv Bhalla, Brisbane (AU); Gill Reid, Southhampton (GB); William Levason, Southhampton (GB)

(73) Assignees: GE HEALTHCARE UK LIMITED, Hampshire (GB); University of Southampton, Hampshire (GB)

( * ) Notice: Subject to any disclaimer, the term of this patent is extended or adjusted under 35 U.S.C. 154(b) by 233 days.

This patent is subject to a terminal disclaimer.

(21) Appl. No.: 14/888,908

(22) PCT Filed: May 2, 2014

(86) PCT No.: PCT/EP2014/058985
§ 371 (c)(1),
(2) Date: Nov. 3, 2015

(87) PCT Pub. No.: WO2014/177689
PCT Pub. Date: Nov. 6, 2014

(65) Prior Publication Data
US 2016/0082136 A1   Mar. 24, 2016

(30) Foreign Application Priority Data

May 3, 2013 (GB) .................................... 1308053

(51) Int. Cl.
| | |
|---|---|
| *A61K 51/00* | (2006.01) |
| *A61M 36/14* | (2006.01) |
| *A61K 51/04* | (2006.01) |
| *C07F 5/00* | (2006.01) |
| *C07D 255/02* | (2006.01) |

(52) U.S. Cl.
CPC ........ *A61K 51/0482* (2013.01); *C07D 255/02* (2013.01); *C07F 5/003* (2013.01)

(58) Field of Classification Search
CPC .... A61K 51/0482; C07F 5/003; C07D 255/02
USPC ......................................................... 424/1.89
See application file for complete search history.

(56) References Cited

U.S. PATENT DOCUMENTS

| | | | |
|---|---|---|---|
| 6,183,744 B1 | 2/2001 | Goldenberg et al. | |
| 2008/0305042 A1* | 12/2008 | Gacek ................ | A61K 51/0402 424/1.89 |
| 2011/0110854 A1* | 5/2011 | McBride .......... | A61K 47/48746 424/1.69 |
| 2014/0377178 A1* | 12/2014 | Bhalla ................ | A61K 51/0482 424/1.69 |

FOREIGN PATENT DOCUMENTS

| | | | |
|---|---|---|---|
| CN | 101854957 A | 10/2010 | |
| CN | 102918031 A | 2/2013 | |
| EP | 0969866 B2 | 2/2009 | |
| EP | 2806901 B1 | 3/2016 | |
| EP | 2991969 A1 | 3/2016 | |
| JP | 2011507863 A | 3/2011 | |
| JP | 2015505533 A | 2/2015 | |
| WO | WO-2006138357 A1 * | 12/2006 | ........... C07D 255/02 |
| WO | 2009/079024 A1 | 6/2009 | |
| WO | 2009079027 | 6/2009 | |
| WO | 2011/068965 A1 | 6/2011 | |
| WO | 2013110615 | 8/2013 | |
| WO | 2014/177689 A1 | 11/2014 | |

OTHER PUBLICATIONS

Wadas et al. Chem. Rev. 2010, 110, 2858-2902.*
Shetty et al. Eur. J. Inorg. Chem. 2010, 5432-5438.*
Laverman et al. J. Nucl. Med. 2010, 51,454-461.*
Penkert et al. Chem. Commun. 1998, 557-558.*
Shetty et al. Chem. Commun. 2011, 47, 9732-9734.*
International Preliminary Report on Patentability Received for PCT Patent Application No. PCT/EP2014/058985, dated Nov. 12, 2015, 8 pages.
Office Action Received for Chinese Patent Application No. 201480024885. 7, dated Nov. 28, 2016, 14 pages (8 pages of English Translation + 6 pages official copy.).
International Search Report issued in PCT/EP2014/058985 dated Jun. 18, 2014.
Weyhermuller et al. "The structure of the S6-symmetric methanol hexamer assembled in a supramolecular hydrophobic cavity", Chemical Communications, 5:557-558 (Jan. 1, 1998).
Sally et al. "Aminoacid N-substituted 1,4,7-triazacyclononane and 1,4,7,10-tetraazacyclododecane Zn2+, Cd2+ and Cu2+ complexes.", Dalton Transactions, 9:1410-1417 (May 7, 2004).
McBride et al. "A novel method of 18F radiolabeling for PET", J Nuclear Medicine, 50(6):991-998 (Jun. 1, 2009).
Tolmachev et al. "Evaluation of a Maleimido Derivative of NOTA for Site-Specific Labeling of Affibody Molecules", Bioconjugate Chemistry, 22(5):894-902 (May 18, 2011).
McBride et al. "Radiofluorination using aluminum-fluoride (Al18F)", EJNMMI Research, 3(1):36-47 (May 8, 2013).
Bhalla et al. "Triaza-macrocyclic complexes of aluminium, gallium and indium halides: fast 18F and 19F incorporation via halide exchange under mild conditions in aqueous solution", Chemical Science, 5(1):381 (Jan. 1, 2014).

(Continued)

*Primary Examiner* — Michael G. Hartley
*Assistant Examiner* — Sean R Donohue
(74) *Attorney, Agent, or Firm* — Jeff B. Vockrodt; Culhane Meadows, PLLC

(57) ABSTRACT

A method of labelling biological molecules with $^{18}F$, via attachment of fluorine to a metal complex, where the metal complex is conjugated to the biological molecule. The invention highlights the incorporation of hydrogen bonding (H-bonding) into the metal complex scaffold, and how this can be utilised to improve the kinetics of fluoride incorporation. Also provided are pharmaceutical compositions, kits and methods of in vivo imaging.

8 Claims, 1 Drawing Sheet

(56) References Cited

OTHER PUBLICATIONS

Japan Notice of Preliminary Rejection for Japanese Patent Application No. 2016-511091, dated Feb. 13, 2018, 4 pages.
Schirrmacher et al. "Recent Developments and Trends in 18F-Radiochemistry: Syntheses and Applications", Mini-Reviews in Organic Chemistry, 2007, pp. 317-329.
McBride et al. "Improved 18F Labeling of Peptides with a Fluoride-Aluminum-Chelate Complex", Bioconjugate Chem, 2010, vol. 21, Issue No. 7 pp. 1331-1340.
Hajela et al. "Highly electron deficient group 3 organometallic complexes based on the 1,4,7-trimethyl-1,4,7-triazacyclononane ligand system", Journal of Organometallic Chemistry, Apr. 1, 1997, vol. 532, Issues 1-2, pp. 45-53.
D'Souza et al. "High-Yielding Aqueous 18F-Labeling of Peptides via Al18F Chelation", Bioconjugate Chem, 2011, vol. 22, pp. 1793-1803.
McBride et al., "The Radiolabeling of Proteins by the [18F]AlF Method", Applied Radiation and Isotopes, vol. 70, 2012, pp. 200-204.
Goodman et al., "Structure-Activity Relationship of a Bitter Diketopiperazine Revisited", Biopolymers, vol. 24, 1985, 137 pages.
Morgan et al., Drug News & Perspectives, vol. 12, No. 3, 1999, pp. 137-145.
Pasqualini et al. "αv Integrins as Receptors for Tumor Targeting by Circulating Ligands", Nature Biotechnology, vol. 15, Issue 6, 1997, pp. 542-546.
Ruoslahti E, "Integrins as Signaling Molecules and Targets for Tumor Therapy", Kidney International, 1997, vol. 51, Issue 5, pp. 1413-1417.
Tone et al, "Structure of Human a2-plasmin Inhibitor Deduced from the cDNA Sequence 1", J Biochem, vol. 102, Issue 5, 1987, pp. 1033-1041.
Hansson et al., "Structure of the Human Beta-Casein Encoding Gene", Gene, vol. 139, Issue 2, 1994, pp. 193-199.
Gutman et al., "Human Fibronectin is Synthesized as a Pre-propolypeptide", FEBS Letters, vol. 207, No. 1, 1986, pp. 145-148.
Dixit et al. "Characterization of a cDNA Encoding the Heparin and Collagen Binding Domains of Human Thrombospondin", Proceedings of the National Academy of Sciences, vol. 83, 1986, pp. 5449-5453.
Doolittle, Russell F., "Fibrinogen and Fibrin", Annual Review of Biochemistry, vol. 53, 1984, pp. 195-229.
Lloyd-Williams et al., "Chemical Approaches to the Synthesis of Peptides and Proteins", CRC Press, 1997.
Hjelstuen et al. "Standardization of Fluorine-18 Manufacturing Processes: New Scientific Challenges for PET", vol. 78, Issue 3, 2011, pp. 307-313.
Jacobson et al. "PET Designated Flouride-18 Production and Chemistry", Current Topics in Medicinal Chemistry, 2010, vol. 10, No. 11, pp. 1048-1059.
Barthomola et al. "Technetium and Gallium Derived Radiopharmaceuticals: Comparing and Contrasting the Chemistry of Two Important Radiometals for the Molecular Imaging Era", Chemical Reviews, vol. 110, Issue 5, 2010, pp. 2903-2920.
Chakraborty et al. "99mTc and 111In-Labeling of Small Biomolecules: Bifunctional Chelators and Related Coordination Chemistry", Current Topics in Medicinal Chemistry, vol. 10, Issue 11, 2010, pp. 1113-1134.
Brechbiel, M. W., "Bifunctional Chelates for Metal Nuclides", Quarterly Journal of Nuclear Medicine and Molecular Imaging, vol. 52, Issue 2, 2008, 166-173.
Weighardt et al. "C2-Symmetric 1,4-Diisopropyl-7-R-1,4,7-Triazacyclononanes", Inorganic Syntheses, 1998, vol. 32, pp. 75-81.
Flassbeck et al. "Synthese von N-phenolat-funktionalisierten Makrocyclen des 1,4,7-Trazacyclononans sowie des 1-Oxa-4,7-diazacyclononans und ihre Komplexchemie mit Eisen(III)", Journal of Inorganic and General Chemistry, vol. 608, Issue No. 2, 1992, pp. 60-68.
Weighardt et al., "New triply hydroxo-bridged complexes of chromium(III), cobalt(III), and rhodium(III): crystal structure of tris(.mu.-hydroxo)bis[(1,4,7-trimethyl-1,4,7-triazacyclononane)chromium(III)] triiodide trihydrate", Inorganic Chemistry, vol. 21, 1982, pp. 3086-3090.
Martin et al., "Synthesis of Selectively Protected tri- and Hexaamine Macrocycles", Journal of Organic Chemistry, vol. 47, Issue 3, 1982, pp. 412-415.
Mahapatra et al., "Structural, Spectroscopic, and Theoretical Characterization of Bis(μ-oxo)dicopper Complexes, Novel Intermediates in Copper-Mediated Dioxygen Activation", Journal of the American Chemical Society, vol. 118, Issue 46, 1996, pp. 11555-11574.
Kuppers et al., "Electron-transfer barriers in cobalt(III) and cobalt(II) bis complexes of 1,4,7-triazacyclononane (tacn) and 1,4,7-trithiacyclononane (ttcn). Crystal structures of [CoII(tacn)2]I2.H2O and of [CoIII(ttcn)2](ClO4)3", Inorganic Chemistry, vol. 25, Issue 14, 1986, pp. 2400-2408.
Clezy et al., "The Chemistry of Pyrrolic Compounds. LXI. Petroporphyrins From the Julia Creek Oil Shale: Further Evidence for the Derivation of Etiotype Petroporphyrins From Chlorophyll", Australian Journal of Chemistry, vol. 42, Issue 6, 1989, pp. 775-786.
Davies et al., "Divergent Pathways in the Intramolecular Reactions between Rhodium-Stabilized Vinylcarbenoids and Pyrroles: Construction of Fused Tropanes and 7-Azabicyclo[4.2.0]octadienes", Journal of Organic Chemistry, 1996, vol. 61, pp. 2305-2313.
Satyamurthy et al., "Electronic Generators for the Production of Positron-Emitter Labeled Radiopharmaceuticals: Where Would PET Be Without Them?", Clinical Positron Imaging, 1999, vol. 2, Issue No. 5, pp. 233-253.
Weyhermuller et al., "Nitrogen versus oxygen co-ordination of carboxamide-functionalized triazacyclononane ligands in transition metal ion complexes", Journal of the Chemical Society, Dalton Transactions, Issue 22, 1998, pp. 3805-3814.
Zhang et al. "Metal ion promoted hydrolysis of nitrile-functionalized triazamacrocycle", Inorganic Chemistry Communications, vol. 9, Issue 3, 2006, pp. 269-272.
Amin et al. "Synthesis and characterization of the yttrium(III) and lutetium(III) complexes of 1,4,7-tris (carbamoylmethyl)-1,4,7-triazacyclononane (TCMT). Crystal structure of [Y(TCMT)(CF3SO3)2(H2O)](CF3SO3)", Inorganica Chimica Acta, 1996, vol. 246, pp. 99-107.
Smith et al. "Inorganic approaches for radiolabelling biomolecules with fluorine-18 for imaging with Positron Emission Tomography", Dalton Transactions, 2011, vol. 40, Issue 23, pp. 6196-6205.
Office Action Received for European Patent Application No. 14723396. 9, dated Jan. 29, 2018, 6 pages.
Plush et al., Aminoacid N-substituted 1,4,7-triazacyclononane and 1,4,7,10-tetrazazcyclododecane Zn2+, Cd2+ and Cu2+ complexes. A preparative, potentiomoetric titration and NMR spectroscopic study, Dalton Trans., 2004, 9, pp. 1410-1417.
McBride et al., "A Novel Method of 18F Radiolabelling for PET," Journal of Nuclear Medicine., 2009, 50(6), 991-998.
Tolmachev et al., "Evaluation of a Maleimido Derivative of NOTA for Site-Specific Labeling of Affibody Molecules," Bioconjugate Chemistry, 2011, 22(5), pp. 894-902.
McBride et al., "Radiofluorination Using Aluminum-Floride (Al18F)," EJNMMI Research, Aug. 5, 2013, 3(1), pp. 36-47.
Japan Office Action corresponding to Japanese Application No. 2016-511091, dated Dec. 4, 2018.
Plush, Sally, et al., "Aminoacid N-substituted 1,4,7-triazacyclononane and 1,4,7,10-tetraazacyclododecane Zn2+, Cd2+ and Cu2+ complexes. A preparative, potentiometric titration and NMR spectroscopic study," Dalton Transactions, 2004, pp. 1410-1417.
McBride, William J., et al., "A Novel Method of 18F Radiolabeling for PET," The Journal of Nuclear Medicine, May 14, 2009, pp. 991-998.
Tolmachev, Vladimir, et al., "Evaluation of a Maleimido Derivative of NOTA for Site-Specific Labeling of Athbody Molecules," Bioconjugate Chemistry, 2011, 22, pp. 894-902.

* cited by examiner

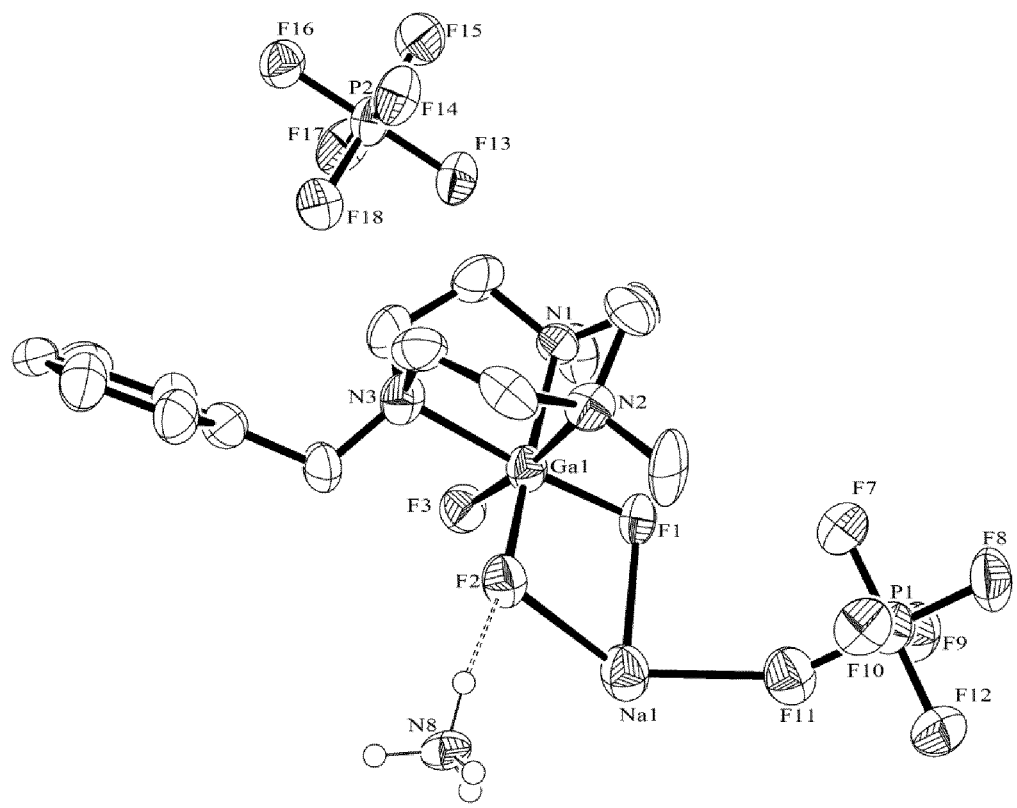
Asymmetric unit of the crystal structure [GaF$_3$(BzMe$_2$-tacn) + Na + NH$_4$][PF$_6$]$_2$

METAL COMPLEXES AND FLUORINATION THEREOF

BACKGROUND OF THE INVENTION

Field of the Invention

The present invention relates to a method of labelling biological molecules with $^{18}$F, via attachment of fluorine to a metal complex, where the metal complex is conjugated to the biological molecule. The invention highlights the incorporation of hydrogen bonding (H-bonding) into the metal complex scaffold, and how this can be utilised to improve the kinetics of fluoride incorporation. Also provided are pharmaceutical compositions, kits and methods of in vivo imaging.

Description of the Related Art

The $^{18}$F radiolabelling of biological molecules, to obtain radiotracers suitable for in vivo imaging is an area of continued interest [Schirrmacher et al. Mini-Rev. Org. Chem., 4(4), 317-329 (2007)]. Whilst there are many methods for direct (single-step) labelling of small molecules with $^{18}$F, these methods are generally not suitable for application to peptides (and larger macromolecules). The presence of amino acids such as lysine and arginine make standard strategies of incorporation of fluoride via nucleophilic substitution difficult, due to:
  (i) hydrogen bonding interactions between the fluoride and these amino acid functionalities, thus reducing the nucleophilicity of the fluoride ion; and/or
  (ii) the requirement to use higher temperatures which can cause the degradation or disruption of the peptide/protein structure.

Inorganic chemistry approaches to improved radiofluorination methods have been reviewed by Smith et al [Dalton Trans., 40, 6196-6205 (2011)].

WO 2009/079024 (McBride et al) discloses an 'inorganic' method of labeling a molecule with $^{18}$F comprising:
  a) reacting the $^{18}$F with a metal to form an $^{18}$F metal complex; and
  b) attaching the $^{18}$F metal complex to a molecule to form one or more $^{18}$F labeled molecules to be administered to a subject.

WO 2009/079024 teaches that suitable metals for the metal complex are selected from aluminium, gallium, indium, lutetium and thallium.

Example 3 of WO 2009/079024 provides the $^{18}$F-labelling of various metal complexes of the chelate-peptide conjugate IMP 272:

DOTA-Gln-Ala-Lys(HSG)-D-Tyr-Lys(HSG)-NH$_2$      IMP 272 where
  DOTA=1,4,7,10-tetraazacyclododecanetetraacetic acid,
  HSG=the histamine succinyl glycyl group.
The $^{18}$F-radiolabelling results reported were: indium (24%), gallium (36%), zirconium (15%), lutetium (37%) and yttrium (2%).

WO 2011/068965 discloses a method of labeling a molecule with $^{18}$F or $^{19}$F comprising attaching a complex of $^{18}$F or $^{19}$F and a group IIIA metal to a chelating moiety, wherein the chelating moiety is conjugated to the molecule or the chelating moiety is later attached to the molecule. WO 2011/068965 states that the metals of group IIIA (aluminium, gallium, indium, and thallium) are suitable for F binding, but that aluminium is in an embodiment.

McBride et al subsequently reported [J. Nucl. Med., 50(6), 991-998 (2009) at page 994] that Ga, In, Zr, Lu and Y do not bind the IMP 272 peptide as well as the aluminium complex, and that the metal complexes of the alternative metals (Ga, In, Zr, Lu and Y) were unstable in water.

More recent publications have focused on aluminium as the metal of choice and optimizing the aluminium chelator used, since the aluminium-fluoride bond is one of the strongest metal-fluoride bonds, and the AlF$_n$ complex is stable in vivo—[McBride et al, Bioconj. Chem., 21(7), 1331-1340 (2010); Bioconj. Chem., 22, 1793-1803 (2011) and Appl. Rad. Isot., 70, 200-204 (2012)]. Preferred chelators are based on the NODA system, with NODA-MPAEM used to conjugate to biomolecules:

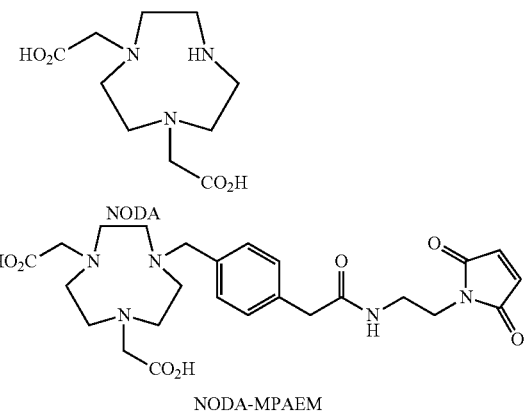

NODA

NODA-MPAEM

The prior art methods of WO 2009/079024, WO 2011/068965 and associated publications do, however have some disadvantages:
  (a) the kinetics of formation of the Al—$^{18}$F bond requires the use of higher temperatures for $^{18}$F-radiolabelling, and many biomolecules are temperature-sensitive;
  (b) the pH range (pH 3.8 to 4.2) for $^{18}$F-radiolabelling these metal complexes is relatively narrow, due to the need to avoid hydrolysis of the aluminium. This will not be compatible with all biomolecules due to acid-sensitive instability or risks of aggregation.

There is therefore still a need for alternative $^{18}$F-radiolabelling methods which permit efficient radiofluorination of a range of biological molecules, under mild conditions (of e.g. temperature and pH). Ideally such methods are suitable for aqueous conditions—since $^{18}$F is typically available as an aqueous solution and some biomolecules may not tolerate organic solvents. The capability of performing the labelling in aqueous or predominantly aqueous conditions will eliminate the requirement to dry the [$^{18}$F] fluoride, which is typically required for traditional $^{18}$F chemistries involving "nucleophilic substitution". This has the benefit that it may further simplify the $^{18}$F radiofluorination chemistry via a reduction of process steps. Reduction of process steps and in particular, the reduction of the radiosynthesis time has benefit in minimising loss of yield due to radioactive decay.

SUMMARY OF THE INVENTION

Embodiments of the present invention provides a versatile method for radiolabelling biomolecules, and in particular peptides:
  (i) at lower temperatures (e.g., room temperature);
  (ii) in aqueous (or predominantly aqueous) conditions;

(iii) in a pH range which can be adjusted or adapted to match the properties of the biomolecule/peptide;
(iv) where the $^{18}$F-labelled agents exhibit high in vivo stability.

The choice of metal ion and chelate scaffold are critical in the design of high affinity fluoride binders. The metal ions and the metal complexes of embodiments of the present invention have several advantages:

(a) the metal ion exhibits a high affinity for fluoride in water and at medium pH;
(b) the metal centre has a coordination number and limited redox ability—which simplifies the speciation and chemistry;
(c) the kinetics of substitution of the ligand being replaced by fluoride ion are fast enough (and sufficiently complete) to take up fluoride in the time available (based upon the half-life of $^{18}$F), but the resulting metal fluoride bond is sufficiently strong that metal-bound fluoride is not easily lost in purification or in vivo;
(d) the precursor for $^{18}$F labelling is a single, well-defined species which can be readily synthesized and purified.

The above characteristics of the metal complexes of embodiments of the present invention mean that the non-radioactive metal complex of interest can be conjugated to the biological targeting moiety, and purified as necessary before the $^{18}$F-radiofluorination step. That is more beneficial over prior art approaches for the reasons described above.

Without wishing to be constrained by theory, the present inventors believe that the pendant $Y^1$ group of the non-radioactive precursor metal complex of Formula (II) will have increased affinity for fluoride compared to the corresponding unfunctionalised (i.e. lacking a pendant $Y^1$ group) precursor metal complex. The functional group $Y^1$ contains a hydrogen bond donor group that is expected to facilitate the approach of fluoride ion to the metal, thus increasing rates of [$^{18}$F]-fluoride uptake—and ultimately producing faster incorporation of $^{18}$F. That in turn provides more efficient $^{18}$F-radiolabelling of biomolecules.

DESCRIPTION OF THE FIGURES

FIG. 1 shows an X-ray crystal structure of [GaF3(BzMe2-tacn)+Na+NH4][PF6]2. Monoclinic, Cc. R1 10.5%. Hexafluorophosphate ions provide charge balance. Ellipsoids are drawn at the 50% probability level. The H-atoms on the BzMe2-tacn ligand are omitted for clarity. The image depicts the H-bonding interaction of the ammonium cation with the MF3 face of the gallium chelate complex. A sodium cation is also interacting in a 2 fashion with the GaF3 face.

DETAILED DESCRIPTION OF THE INVENTION

In a first aspect, embodiments of the present invention provides an imaging agent which comprises an $^{18}$F-labelled compound of Formula I:

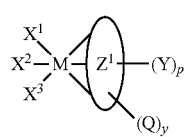

(I)

where:
$X^1$, $X^2$ and $X^3$ are independently Br, Cl, $^{19}$F or $^{18}$F, with the proviso that at least one of $X^1$, $X^2$ and $X^3$ is $^{18}$F;
M is $Al^{3+}$, $Ga^{3+}$, $In^{3+}$, $Sc^{3+}$, $Y^{3+}$, $Ho^{3+}$, $Er^{3+}$, $Tm^{3+}$, $Yb^{3+}$ or $Lu^{3+}$;
$Z^1$ is a tridentate triamine chelating agent wherein all 3 amine donors are bound to M, wherein $Z^1$ has at least one Y group, and optionally also a Q group covalently conjugated thereto;
p is 1, 2 or 3;
y is 0 or 1;
Y is independently -$(A^1)_x$-$Y^1$ or -$(A^1)_x$-$Y^1$-Q where each $A^1$ is independently —$CH_2$— or —O—, provided that Y does not comprise any —O—O— bonds;
wherein x is an integer of value 1 to 6; and
$Y^1$ is $NHR^a$, —$NH(CH_2)_2NHR^a$, —$NH(CH_2)_3NHR^a$, —(C=O)$NHR^a$, —NH(C=O)$R^a$, —NH(C=NH)$NHR^a$, —$OR^a$, a $Y^2$ group or a $Y^3$ group;
$Y^2$ is:

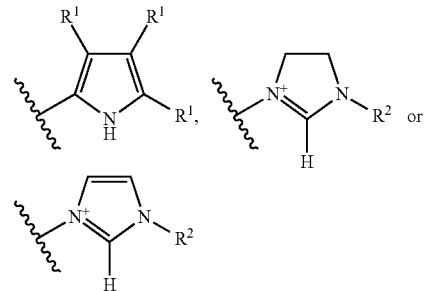

$Y^3$ is Arg, Lys, Asn, Gln, Ser, Thr or Tyr;
wherein $R^a$ is independently H, $C_{1-4}$ alkyl, $C_{2-4}$ alkenyl, $C_{2-4}$ alkynyl, $C_{2-4}$ alkoxyalkyl or $C_{1-4}$ hydroxyalkyl;
and wherein each $R^1$ is independently $C_{1-4}$ alkyl, $C_{2-4}$ alkoxyalkyl or $C_{1-4}$ hydroxyalkyl;
and $R^2$ is independently H or $C_{1-4}$ alkyl; or Si($C_{1-4}$ alkyl)$_3$;
Q is -L-[BTM];
L is a synthetic linker group of formula -$(A)_m$- wherein each A is independently —$CR_2$—, —CR=CR—, —C≡C—, —$CR_2CO_2$—, —$CO_2CR_2$—, —NRCO—, —CONR—, —CR=N—O—, —NR(C=O)NR—, —NR(C=S)NR—, —$SO_2NR$—, —$NRSO_2$—, —$CR_2OCR_2$—, —$CR_2SCR_2$—, —$CR_2NRCR_2$—, a $C_{4-8}$ cycloheteroalkylene group, a $C_{4-8}$ cycloalkylene group, —Ar—, —NR—Ar—, —O—Ar—, —Ar—(CO)—, an amino acid, a sugar or a monodisperse polyethyleneglycol (PEG) building block, wherein each R is independently chosen from H, $C_{1-4}$ alkyl, $C_{2-4}$ alkenyl, $C_{2-4}$ alkynyl, $C_{2-4}$ alkoxyalkyl or $C_{1-4}$ hydroxyalkyl;
m is an integer of value 1 to 20;
each Ar is independently a $C_{5-12}$ arylene group, or a $C_{3-12}$ heteroarylene group;
BTM is a biological targeting moiety.

The imaging agents of Formula I of the first aspect comprise a metal complex of a non-radioactive trivalent metal ion (M), i.e. where the metal is in the M(III) oxidation state ($M^{3+}$). By the term "metal complex" is meant a coordination complex of a metal. Suitable such metal complexes comprise the chelating agent, $Z^1$. The metal complex of Formula I has the 3 amine donors of the chelating agent $Z^1$ and the 3 halogens $X^1$, $X^2$ and $X^3$ bound to M. Suitable metals of the invention (M) include aluminium, gallium, indium, scandium, yttrium, holmium, erbium, terbium, ytterbium or lutetium.

By the term "imaging agent" is meant a compound suitable for imaging the mammalian body. The mammal may be an intact mammalian body in vivo, and more particularly may be a human subject. Such imaging agents are designed to have minimal pharmacological effect on the mammalian subject to be imaged. The imaging agent can be administered to the mammalian body in a minimally invasive manner, i.e. without a substantial health risk to the mammalian subject when carried out under professional medical expertise. Such minimally invasive administration may include intravenous administration into a peripheral vein of the subject, without the need for local or general anaesthetic.

The term "in vivo imaging" as used herein refers to those techniques that non-invasively produce images of all or part of an internal aspect of a mammalian subject. In an embodiment, the imaging technique of the present invention is positron emission tomography (PET).

The terms "comprising" or "comprises" have their conventional meaning throughout this application and imply that the agent or composition must have the essential features or components listed, but that others may be present in addition. The term 'comprising' includes as a subset "consisting essentially of" which means that the composition has the components listed without other features or components' being present.

By the term "biological targeting moiety" (BTM) is meant a compound which, after administration, is taken up selectively or localises at a particular site of the mammalian body in vivo. Such sites may for example be implicated in a particular disease state or be indicative of how an organ or metabolic process is functioning.

In Formula I, the Y and/or Q groups are conjugated to either the backbone of the chelating agent ($Z^1$), or to the N donor atoms of $Z^1$. When Y is -($A^1$)$_x$-$Y^1$-Q, that means that the BTM and the $Y^1$ group are attached as part of the same substituent on $Z^1$.

EXAMPLES

In Formula I, may be one Q group is present. Q may be located at Y, i.e. y is 0, and Y is -($A^1$)$_x$-$Y^1$-Q. It is particularly convenient that, when the BTM is a peptide, $Y^1$ is a $Y^3$ group so that potentially both $Y^1$ and BTM may form part of the same peptide conjugated to the chelator $Z^1$.

In Formula I, each Y group in an embodiment present may be covalently conjugated to a different amine donor atom of $Z^1$.

In Formula I, $Y^1$ may be an amide of formula —(C═O)NHR$^a$ or —NH(C═O)R$^a$, or a $Y^2$ pyrrole group of formula $Y^{2a}$:

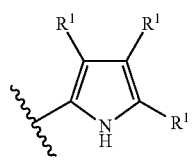

$Y^{2a}$

In an embodiment, $Y^{2a}$ pyrrole groups have each $R^1$═$C_{1-4}$ alkyl, methyl or dimethyl-ethyl.

The BTM may be of synthetic or natural origin, but in an embodiment is synthetic. The term "synthetic" has its conventional meaning, i.e. man-made as opposed to being isolated from natural sources eg. from the mammalian body. Such compounds have the advantage that their manufacture and impurity profile can be fully controlled. Monoclonal antibodies and fragments thereof of natural origin are therefore outside the scope of the term 'synthetic' as used herein. In an embodiment, the molecular weight of the BTM is up to 30,000 Daltons. In another embodiment, the molecular weight is in the range 200 to 20,000 Daltons, more particularly 300 to 18,000 Daltons, with 400 to 16,000 Daltons being the molecular weight in an embodiment. In an embodiment, when the BTM is a non-peptide, the molecular weight of the BTM is up to 3,000 Daltons, more particularly 200 to 2,500 Daltons, more particularly 300 to 2,000 Daltons, with 400 to 1,500 Daltons being the molecular weight in an embodiment.

In an embodiment, the biological targeting moiety comprises: a 3-100 mer peptide, peptide analogue, peptoid or peptide mimetic which may be a linear or cyclic peptide or combination thereof; a single amino acid; an enzyme substrate, enzyme antagonist enzyme agonist (including partial agonist) or enzyme inhibitor; receptor-binding compound (including a receptor substrate, antagonist, agonist or substrate); oligonucleotides, or oligo-DNA or oligo-RNA fragments. The enzyme and/or receptor may be endogenous to the mammalian subject.

By the term "peptide" is meant a compound comprising two or more amino acids, as defined below, linked by a peptide bond (ie. an amide bond linking the amine of one amino acid to the carboxyl of another). The term "peptide mimetic" or "mimetic" refers to biologically active compounds that mimic the biological activity of a peptide or a protein but are no longer peptidic in chemical nature, that is, they no longer contain any peptide bonds (that is, amide bonds between amino acids). Here, the term peptide mimetic is used in a broader sense to include molecules that are no longer completely peptidic in nature, such as pseudo-peptides, semi-peptides and peptoids. The term "peptide analogue" refers to peptides comprising one or more amino acid analogues, as described below. See also *Synthesis of Peptides and Peptidomimetics*, M. Goodman et al, Houben-Weyl E22c, Thieme.

By the term "amino acid" is meant an L- or D-amino acid, amino acid analogue (e.g. naphthylalanine) or amino acid mimetic which may be naturally occurring or of purely synthetic origin, and may be optically pure, i.e. a single enantiomer and hence chiral, or a mixture of enantiomers. Conventional 3-letter or single letter abbreviations for amino acids are used herein. The amino acids of the present invention may be optically pure. By the term "amino acid mimetic" is meant synthetic analogues of naturally occurring amino acids which are isosteres, i.e. have been designed to mimic the steric and electronic structure of the natural compound. Such isosteres are well known to those skilled in the art and include but are not limited to depsipeptides, retro-inverso peptides, thioamides, cycloalkanes or 1,5-disubstituted tetrazoles [see M. Goodman, Biopolymers, 24, 137, (1985)]. Radiolabelled amino acids such as tyrosine, histidine or proline are known to be useful in vivo imaging agents.

In an embodiment, when the BTM is an enzyme substrate, enzyme antagonist, enzyme agonist, enzyme inhibitor or receptor-binding compound it is a non-peptide, and more more particularly is synthetic. By the term "non-peptide" is meant a compound which does not comprise any peptide bonds, ie. an amide bond between two amino acid residues. Suitable enzyme substrates, antagonists, agonists or inhibitors include glucose and glucose analogues; fatty acids, or elastase, Angiotensin II or metalloproteinase inhibitors. The enzyme of the enzyme substrate, antagonist, agonist or inhibitor may be endogenous to the mammalian subject. Suitable synthetic receptor-binding compounds include estradiol, estrogen, progestin, progesterone and other steroid hormones; ligands for the dopamine D-1 or D-2 receptor, or dopamine transporter such as tropanes; and ligands for the serotonin receptor. The receptor of the receptor-binding compound may be endogenous to the mammalian subject.

In an embodiment, the BTM is a 3-100 mer peptide or peptide analogue. When the BTM is a peptide, it is it may be a 4-30 mer peptide, and more particularly a 5 to 28-mer peptide.

When the BTM is an enzyme substrate, enzyme antagonist, enzyme agonist or enzyme inhibitor, biological targeting molecules in an embodiment of the present invention are synthetic, drug-like small molecules i.e. pharmaceutical molecules. More particularly, dopamine transporter ligands such as tropanes; fatty acids; dopamine D-2 receptor ligands; benzamides; amphetamines; benzylguanidines, iomazenil, benzofuran (IBF) or hippuric acid. Tropane agents are described by Morgan and Nowotnik [Drug News Perspect., 12(3), 137-145 (1999).

When the BTM is a peptide, such peptides may include: somatostatin, octreotide and analogues, peptides which bind to the ST receptor, where ST refers to the heat-stable toxin produced by *E. coli* and other micro-organisms; bombesin; vasoactive intestinal peptide; neurotensin; laminin fragments, N-formyl chemotactic peptides for targeting sites of leucocyte accumulation, Platelet factor 4 (PF4) and fragments thereof, RGD (Arg-Gly-Asp)-containing peptides, which may eg. target angiogenesis [R. Pasqualini et al., Nat Biotechnol. 1997 June; 15(6):542-6]; [E. Ruoslahti, Kidney Int. 1997 May; 51(5):1413-7]. peptide fragments of $\alpha_2$-antiplasmin, fibronectin or beta-casein, fibrinogen or thrombospondin. The amino acid sequences of $\alpha_2$-antiplasmin, fibronectin, beta-casein, fibrinogen and thrombospondin can be found in the following references: $\alpha_2$-antiplasmin precursor [M. Tone et al., J. Biochem, 102, 1033, (1987)]; beta-casein [L. Hansson et al, Gene, 139, 193, (1994)]; fibronectin [A. Gutman et al, FEBS Lett., 207, 145, (1996)]; thrombospondin-1 precursor [V. Dixit et al, Proc. Natl. Acad. Sci., USA, 83, 5449, (1986)]; R. F. Doolittle, Ann. Rev. Biochem., 53, 195, (1984); peptides which are substrates or inhibitors of angiotensin, such as: angiotensin II or Angiotensin I.

In an embodiment BTM peptides are RGD peptides. A more particular RGD peptide comprises the fragment:

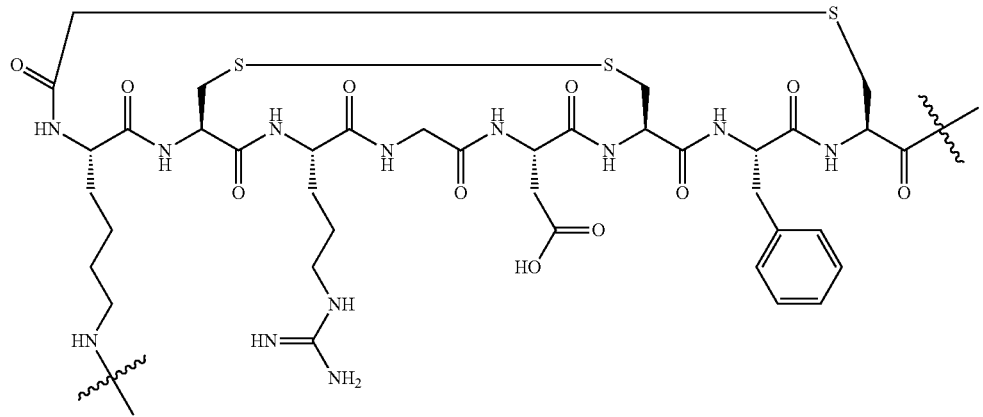 [SMILES: *NCCCC[C@@H]1NC(=O)CSC[C@@H](C(*)=O)NC(=O)[C@H](Cc2ccccc2)NC(=O)[C@@H]2CSSC[C@H](NC1=O)C(=O)N[C@@H](CCCNC(=N)N)C(=O)NCC(=O)N[C@@H](CC(=O)O)C(=O)N2]

A Another RGD peptide is when the BTM is a peptide of formula (A):

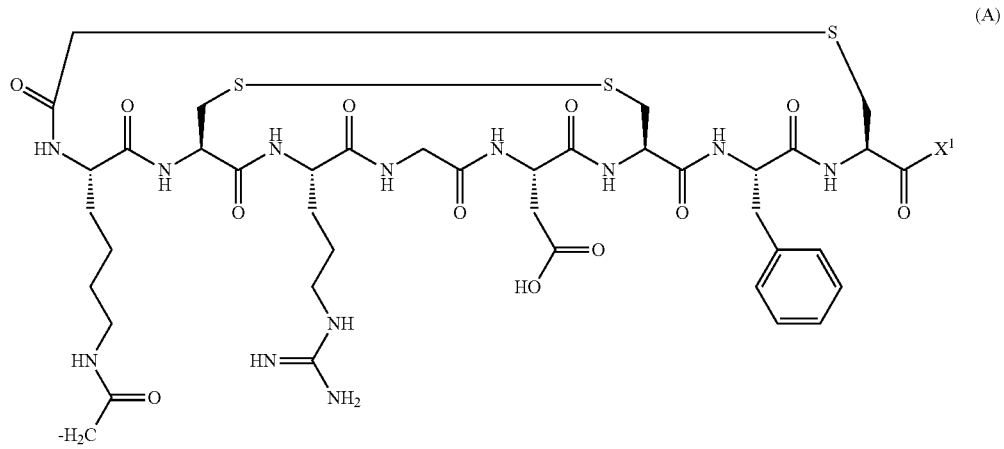

(A)

wherein $X^1$ is either —$NH_2$ or

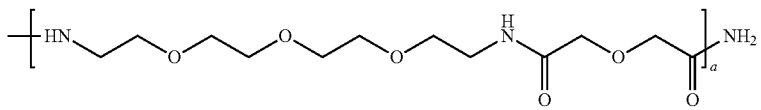

wherein a is an integer of from 1 to 10.
In Formula A, in an embodiment, a is 1.

When the BTM is a peptide, one or both termini of the peptide (in an embodiment, both), have conjugated thereto a metabolism inhibiting group ($M^{IG}$). Having both peptide termini protected in this way is important for in vivo imaging applications, since otherwise rapid metabolism would be expected with consequent loss of selective binding affinity for the BTM peptide. By the term "metabolism inhibiting group" ($M^{IG}$) is meant a biocompatible group which inhibits or suppresses enzyme, especially peptidase such as carboxypeptidase, metabolism of the BTM peptide at either the amino terminus or carboxy terminus. Such groups are particularly important for in vivo applications, and are well known to those skilled in the art and are suitably chosen from, for the peptide amine terminus:

N-acylated groups —NH(C=O)$R^G$ where the acyl group —(C=O)$R^G$ has $R^G$ chosen from: $C_{1-6}$ alkyl, $C_{3-10}$ aryl groups or comprises a polyethyleneglycol (PEG) building block. Suitable PEG groups are described for the linker group ($L^1$), below. In an embodiment, PEG groups are the biomodifiers of Formulae Bio1 or Bio2 (below). In an embodiment amino terminus $M^{IG}$ groups are acetyl, benzyloxycarbonyl or trifluoroacetyl, for example, more particularly acetyl.

Suitable metabolism inhibiting groups for the peptide carboxyl terminus include: carboxamide, tert-butyl ester, benzyl ester, cyclohexyl ester, amino alcohol or a polyethyleneglycol (PEG) building block. A suitable $M^{IG}$ group for the carboxy terminal amino acid residue of the BTM peptide is where the terminal amine of the amino acid residue is N-alkylated with a $C_{1-4}$ alkyl group, such as a methyl group. In an embodiment, $M^{IG}$ groups are carboxamide or PEG, and more particularly such groups are carboxamide.

When the linker group (L) comprises a peptide chain of 1 to 10 amino acid residues, the amino acid residues may be chosen from glycine, lysine, arginine, aspartic acid, glutamic

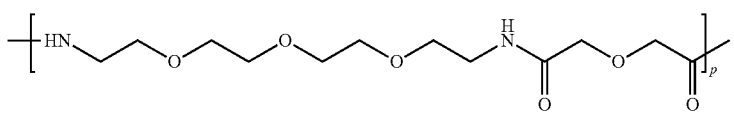

acid or serine. When L comprises a PEG moiety, it may comprise units derived from oligomerisation of the monodisperse PEG-like structures of Formulae Bio1 or Bio2:

(Bio1)
17-amino-5-oxo-6-aza-3,9,12,15-tetraoxaheptadecanoic acid of Formula Bio1 wherein p is an integer from 1 to 10. Alternatively, a PEG-like structure based on a propionic acid derivative of Formula Bio2 can be used:

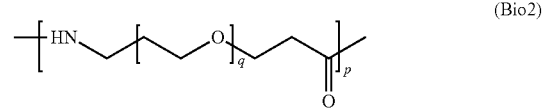

(Bio2)

where p is as defined for Formula Bio1 and q is an integer from 3 to 15.

In Formula Bio2, p may be 1 or 2, and q may be 5 to 12.
When the linker group does not comprise PEG or a peptide chain, L groups have a backbone chain of linked atoms which make up the -(A)$_m$- moiety of 2 to 10 atoms, more particularly 2 to 5 atoms, and most particularly with 2 or 3 atoms.

BTM peptides which are not commercially available can be synthesised by solid phase peptide synthesis as described in P. Lloyd-Williams, F. Albericio and E. Girald; *Chemical Approaches to the Synthesis of Peptides and Proteins*, CRC Press, 1997.

In an embodiment, the chelating agent $Z^1$ of the first aspect is of Formula $Z^a$, $Z^b$ or $Z^c$:

(Z$^a$)

(Z$^b$)

-continued

(Z$^c$)

where each $R^3$ is independently H, $C_{1-4}$ alkyl, $C_{2-4}$ alkoxyalkyl, $C_{1-4}$ hydroxyalkyl, a Y group or a Q group;
each f is independently 1 or 2.

In Formula $Z^a$, in an embodiment, each f=1.

In an embodiment, chelators of Formula ($Z^a$) are of Formula $Z^{aa}$ or $Z^{ab}$:

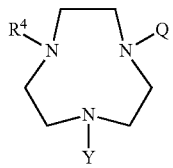

(Z$^{aa}$)

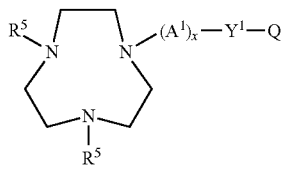

(Z$^{ab}$)

where $R^4$ is H, $C_{1-4}$ alkyl, $C_{2-4}$ alkoxyalkyl, $C_{1-4}$ hydroxyalkyl or a Y group;
$R^5$ is H, $C_{1-4}$ alkyl, $C_{2-4}$ alkoxyalkyl or $C_{1-4}$ hydroxyalkyl.

In Formulae $Z^a$, $Z^b$, $Z^c$, $Z^{aa}$ and $Z^{ab}$, variables x, Y and Q, and some aspects thereof are as defined for Formula I.

In an embodiment, chelators of Formula $Z^{aa}$ are:

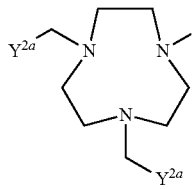 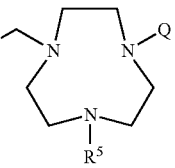

where $Y^{2a}$ and $R^5$ are as defined above.

In an alternative embodiment, the Q group is attached to the chelator backbone as shown in Formula $Z^d$:

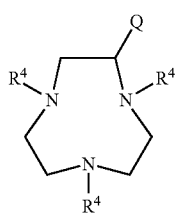

(Z$^d$)

where $R^4$ in Formula $Z^d$ is as defined for Formula $Z^{aa}$.

In Formula I, $X^1$, $X^2$ and $X^3$ may be independently Cl, $^{19}$F or $^{18}$F. More particularly, two of $X^1$, $X^2$ and $X^3$ are $^{19}$F, and the third is $^{18}$F.

In Formula I, M may be $Al^{3+}$, $Ga^{3+}$, $In^{3+}$, $Sc^{3+}$ or $Y^{3+}$; more particularly $Ga^{3+}$, $In^{3+}$, $Sc^{3+}$ or $Y^{3+}$; more particularly $Ga^{3+}$ or $In^{3+}$; with $Ga^{3+}$ being the ideal.

The imaging agent may be provided in sterile form, i.e. in a form suitable for mammalian administration as is described in the fifth aspect (below).

The imaging agents of the first aspect can be obtained as described in the second aspect (below).

In a second aspect, embodiments of the present invention provides a method of preparation of the imaging agent of the first aspect, which method comprises reaction of a precursor with a supply of [$^{18}$F]-fluoride or [$^{18}$F]NaF, optionally in the presence of [$^{19}$F]-fluoride, in a suitable solvent,
wherein the precursor comprises a metal complex of a chelator of Formula II:

(II)

where $Z^1$, Y, Q, p and q and some embodiments thereof are as defined in the first aspect;
and where the metal is chosen from: $Al^{3+}$, $Ga^{3+}$, $In^{3+}$, $Sc^{3+}$, $Y^{3+}$, $Ho^{3+}$, $Er^{3+}$, $Tm^{3+}$, $Yb^{3+}$ or $Lu^{3+}$.

The metal of the metal complex precursor can be radioactive or non-radioactive. When the metal is radioactive, suitable radiometal isotopes include $^{67}$Ga, $^{68}$Ga and $^{111}$In. The metal of the metal complex of the precursor may be non-radioactive. Hence, the precursor used in the second aspect may be non-radioactive.

The [$^{18}$F]-fluoride may either be:
(i) delivered directly from a cyclotron and formulated using an ion exchange cartridge and appropriate eluent; or
(ii) in the form of GMP [$^{18}$F]NaF produced on an automated platform in a GMP facility.

The production of [$^{18}$F]-fluoride suitable for radiopharmaceutical applications is well-known in the art, and has been reviewed by Hjelstuen et al [Eur. J. Pharm. Biopharm., 78(3), 307-313 (2011)], and Jacobson et al [Curr. Top. Med. Chem., 10(11), 1048-1059 (2010)]. [$^{18}$F]NaF can be produced using an "automated synthesizer" as described in the sixth aspect (below).

The "suitable solvent" includes: acetonitrile, a $C_{1-4}$ alkylalcohol, dimethylformamide, tetrahydrofuran, or dimethylsulfoxide, or aqueous mixtures of any thereof, or water. Aqueous buffers can be used in the pH range of 4-8, more particularly 5-7. solvent is aqueous in nature, and is more particularly a biocompatible carrier solvent as defined in the fourth aspect (below).

The $^{19}$F-carrier (when used) may be in the form of:
(a) alkaline metal salt (eg NaF, KF, CsF etc); or
(b) in the presence of "non-metallic counter ions" (eg [$R_4N$]F where R=alkyl), [$Ar_4P$]F; [$Ar_3S$]F
(c) metal cryptand counterions eg [K(kryptofix 2.2.2)]F, [Na(kryptofix 2.2.2)]F, [N(18-crown-6)]F etc.

The metal complex precursor of the second aspect may be of Formula III:

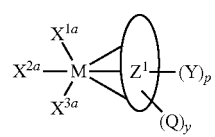

(III)

where M, $Z^1$, Y, Q, p and y are as defined in the first aspect; and
$X^{1a}$, $X^{2a}$ and $X^{3a}$ are independently Br or Cl.

In embodiments of M, $Z^1$, Y, Q, p and y in Formula III are as defined in the first aspect (above). In the precursor of Formula III, one Q group may be present. For the precursor of Formula III, $X^{1a}=X^{2a}=X^{3a}=Cl$ in an embodiment. The precursor may be provided in sterile form, to facilitate the preparation of imaging agents in pharmaceutical composition form as is described in the fifth aspect (below).

The precursor used in the second aspect can be obtained as described in the fourth aspect (below).

In a third aspect, the present invention provides a chelating agent of Formula IIA:

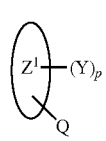

(IIA)

where $Z^1$, Y, Q and p are as defined in the first aspect.

In some embodiments of $Z^1$, Y, Q, p and q in the third aspect are as defined in the first aspect. In particular, the chelator may be of Formula $Z^a$, $Z^b$ or $Z^c$, $Z^{aa}$ and embodiments thereof as described above. The chelator of Formula II has a single Q group conjugated thereto, i.e. Formula IIA is a subset of Formula II, wherein y is 1.

The chelating agent of the third aspect can be obtained as described in the fourth aspect (below).

In a fourth aspect, the present invention provides a metal complex of the chelating agent of Formula II of the third aspect, where the metal is $Al^{3+}$, $Ga^{3+}$, $In^{3+}$, $Sc^{3+}$, $Y^{3+}$, $Ho^{3+}$, $Er^{3+}$, $Tm^{3+}$, $Yb^{3+}$ or $Lu^{3+}$.

In aspects of the chelating agent in the fourth aspect are as described in the first and third aspects (above).

The metal of the metal complex of the fourth aspect can be radioactive or non-radioactive. When the metal is radioactive, suitable radiometal isotopes include $^{67}Ga$, $^{68}Ga$ and $^{111}In$. The metal of the metal complex of the fourth aspect may be non-radioactive. Most particularly, the metal complex may be the precursor of Formula III as defined in the second aspect (above). The precursor of Formula III may comprise one Q group, where Q comprises a BTM which is chosen from: a 3-100 mer peptide, an enzyme substrate, an enzyme antagonist an enzyme agonist, an enzyme inhibitor or a receptor-binding compound.

Aspects of the precursor of Formula III may be as described in the second aspect of the invention (above). Aspects of the Q group and BTM in the fourth aspect may be as described in the first aspect of the invention (above). The precursor may be "in a form suitable for mammalian administration" as defined below, more particularly in lyophilized form.

An embodiment of a method of preparation of the precursor is via metal complex formation with the chelator of Formula II is described in the second aspect. The chelator can be prepared by literature methods, and modifications thereof. When Q is absent, the precursor metal complex can be obtained by conventional metal coordination chemistry—using analogous metal complexation conditions to those described for the bifunctional chelate approach. See also Bhalla et al [Chem. Sci., 5, 381-391 (2014)] and references therein, plus the present supporting Examples. When Q is present, the precursor can be obtained by the bifunctional chelate approach. The term "bifunctional chelate" has its conventional meaning, and refers to a chelating agent having covalently attached thereto a pendant functional group. The functional group is used as a reactive site to attach the chelator to the BTM. The bifunctional chelate approach and associated syntheses have been described by Bartholoma et al [Chem. Rev., 110(5), 2903-2920 (2010)]; Chakraborty et al [Curr. Top. Med. Chem., 10(11), 1113-1134 (2010)] and Brechbiel et al [Quart. J. Nucl. Med. Mol. Imaging, 52(2), 166-173 (2008)]. The functional group in an embodiment of the present invention may be an amine, carboxylic acid or activated ester, more particularly a primary amine or an activated ester. Bifunctional chelators having a pendant amine functional group can be conjugated to the carboxyl group of a BTM. Bifunctional chelators having a carboxyl or activated ester functional group can be conjugated to an amine group of a BTM.

When preparing Ga(III) complexes, the use of anhydrous $GaCl_3$ as the Ga(III) source in the labelling work is challenging due to the high sensitivity of this compound to hydrolysis, which makes weighing out and manipulating the very small quantities necessary for labelling work difficult. In an embodiment, a source of Ga(III) is $Ga(NO_3)_3 \cdot nH_2O$ (commercially available from Sigma-Aldrich). The composition of the salt has been determined as the nona-hydrate. $Ga(NO_3)_3 \cdot nH_2O$ is soluble and stable in aqueous media (pH ~3). This has the advantage of being able to deliver small quantities of the salt and subsequently diluting it in aqueous or buffered solution to the desired concentration, without risk of degradation. A further advantage is that the nitrate anion can be readily exchanged for fluoride under radiolabelling conditions. Finally, $Ga(NO_3)_3$ in dilute $NHO_3$ forms the hexa-aqu species $[Ga(H_2O)_6]^{3+}$, which is the reference standard used in $^{71}Ga$ NMR spectroscopy (δ=0). This has the additional advantage of permitting tracking the course of reactions using $^{71}Ga$ NMR.

By the term "activated ester" or "active ester" is meant an ester derivative of the associated carboxylic acid which is designed to be a better leaving group, and hence permit more facile reaction with nucleophile, such as amines. Examples of suitable active esters are: N-hydroxysuccinimide (NHS); sulfo-succinimidyl ester; pentafluorophenol; pentafluorothiophenol; para-nitrophenol; hydroxybenzotriazole and PyBOP (i.e. benzotriazol-1-yl-oxytripyrrolidinophosphonium hexafluorophosphate). In an embodiment active esters are N-hydroxysuccinimide or pentafluorophenol esters, especially N-hydroxysuccinimide esters.

When a bifunctional chelator having a carboxyl functional group is conjugated to an amine group of a BTM, an activating agent is used. By the term "activating agent" is meant a reagent used to facilitate coupling between an amine and a carboxylic acid to generate an amide. Suitable such activating agents are known in the art and include carbodiimides such as EDC [N-(3-dimethylaminopropyl)-N'-ethylcarbodiimide and N,N'-dialkylcarbodiimides such as dicyclohexylcarbodiimide or diisopropylcarbodiimide; and triazoles such as HBTU [O-(benzotriazol-1-yl)-N,N,N,N'-tetramethyluronium hexafluorophosphate], HATU [O-(7-azabenzotriazol-1-yl)-N,N,N,N'-tetramethyluronium hexafluorophosphate], and PyBOP [benzotriazol-1-yloxy) tripyrrolidinophosphonium hexafluorophosphate]. Such activating agents are commercially available. Further details are given in *March's Advanced Organic Chemistry, 5th* Edition, pages 508-510, Wiley Interscience (2001). In an embodiment, an activating agent may be EDC.

The chelator-BTM conjugates of the $Z^a$ type can be prepared using analogous chemistry to McBride et al [Bioconj. Chem., 21(7), 1331-1340 (2010); Bioconj. Chem., 22, 1793-1803 (2011) and Appl. Rad. Isot., 70, 200-204 (2012)], e.g:

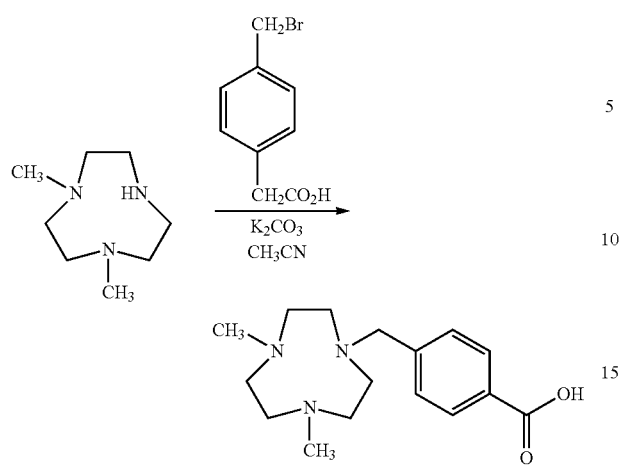

The starting material 1,4-dimethyl-tacn can be obtained by the method of Wieghardt et al [Inorg. Synth., 32, 75-81 (1998); Z. Anorg. Allg. Chem., 608, 60-68 (1992)]. Tacn and Me₃-tacn are commercially available. Me₃-tacn can also be obtained by the method of Wieghardt et al [Inorg Chem., 21, 3086 (1982)]. N-functionalised tacn chelators can be obtained by the method of Martin et al [J. Org. Chem., 47, 412 (1982)] or Mahapatra et al [J. Am. Chem. Soc., 118, 11555 (1996)]. Backbone-functionalised tacn chelators are described by Kuppers et al [Inorg. Chem., 25, 2400 (1986)].

By the term "protecting group" is meant a group which inhibits or suppresses undesirable chemical reactions, but which is designed to be sufficiently reactive that it may be cleaved from the functional group in question under mild enough conditions that do not modify the rest of the molecule. After deprotection the desired product is obtained. Amine protecting groups are well known to those skilled in the art and are suitably chosen from: Boc (where Boc is tert-butyloxycarbonyl), Fmoc (where Fmoc is fluorenylmethoxycarbonyl), trifluoroacetyl, allyloxycarbonyl, Dde [i.e. 1-(4,4-dimethyl-2,6-dioxocyclohexylidene)ethyl] or Npys (i.e. 3-nitro-2-pyridine sulfenyl). Suitable thiol protecting groups are Trt (Trityl), Acm (acetamidomethyl), t-Bu (tert-butyl), tert-Butylthio, methoxybenzyl, methylbenzyl or Npys (3-nitro-2-pyridine sulfenyl). The use of further protecting groups are described in *Protective Groups in Organic Synthesis*, 4th Edition, Theorodora W. Greene and Peter G. M. Wuts, [Wiley Blackwell, (2006)]. In an embodiment pyrrole protecting groups are Boc and Fmoc, more particularly Boc.

Amide functionalized chelators are described in Table 1 and the supporting Examples (see below). Pyrrole-functionalised chelators can be prepared as described in Scheme 1 (below):

Scheme 1

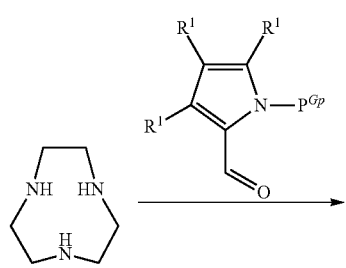

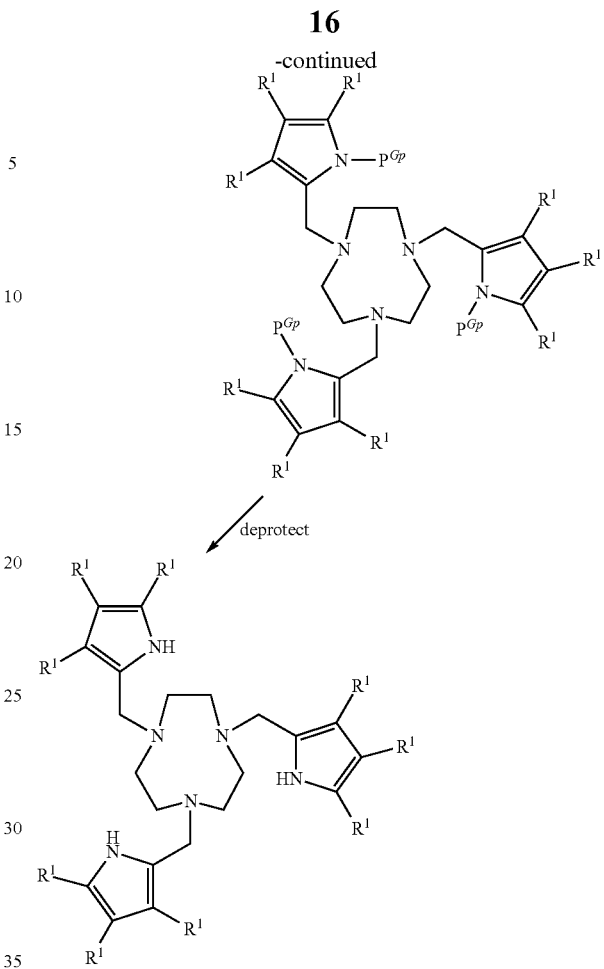

where: $R^1$ is independently $C_{1-4}$ alkyl, $C_{2-4}$ alkoxyalkyl or $C_{1-4}$ hydroxyalkyl;
$P^{Gp}$ is a protecting group.

The alkylated pyrrole aldehyde 3,5-dimethyl-4-ethyl-pyrrole-2-carboxaldehyde is commercially available (Sigma-Aldrich). 3,4,5-Trimethylpyrrole-2-carboxaldehyde, 3,5-dimethyl-4-ethyl-pyrrole-2-carboxaldehyde and 4,5-dimethyl-3-ethyl-pyrrole-2-carboxaldehyde can be prepared as described by Clezy et al [Aust. J. Chem., 42, 775-786 (1989)]. The condensation of the pyrrole aldehyde with tacn can be carried out by first protecting the pyrrole by the method of Davies et al for 1-(tert-butoxycarbonyl)pyrrole-2-carboxaldehyde [J. Org. Chem., 61, 2305-2313 (1996)], followed by reductive amination [*March's Advanced Organic Chemistry*, 5th Edition, pages 1187-1189, Wiley Interscience (2001)]. The deprotection is carried out by standard methods as described in Greene and Wuts (above). The synthesis of Scheme 1 can be readily adapted to systems wherein alternative N-functionalised tacn starting materials are used so that one or two pyrrole substituents are attached.

In a fifth aspect, the present invention provides a radiopharmaceutical composition which comprises the imaging agent of the first aspect, together with a biocompatible carrier, in a form suitable for mammalian administration.

In aspects of the imaging agent in the fifth aspect are as described in the first aspect of the present invention (above).

By the phrase "in a form suitable for mammalian administration" is meant a composition which is sterile, pyrogen-free, lacks compounds which produce toxic or adverse effects, and is formulated at a biocompatible pH (approximately pH 4.0 to 10.5). Such compositions lack particulates which could risk causing emboli in vivo, and are formulated so that precipitation does not occur on contact with biological fluids (e.g. blood). Such compositions also contain only biologically compatible excipients, and may be particularly isotonic.

The "biocompatible carrier" is a fluid, especially a liquid, in which the imaging agent can be suspended or may be dissolved, such that the composition is physiologically tolerable, i.e. can be administered to the mammalian body without toxicity or undue discomfort. The biocompatible carrier is suitably an injectable carrier liquid such as sterile, pyrogen-free water for injection; an aqueous solution such as saline (which in an embodiment may be balanced so that the final product for injection is isotonic); an aqueous buffer solution comprising a biocompatible buffering agent (e.g. phosphate buffer); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like). The biocompatible carrier may be pyrogen-free water for injection, isotonic saline or phosphate buffer.

The imaging agents and biocompatible carrier are each supplied in suitable vials or vessels which comprise a sealed container which permits maintenance of sterile integrity and/or radioactive safety, plus optionally an inert headspace gas (eg. nitrogen or argon), whilst permitting addition and withdrawal of solutions by syringe or cannula. In an embodiment such container is a septum-sealed vial, wherein the gas-tight closure is crimped on with an overseal (typically of aluminium). The closure is suitable for single or multiple puncturing with a hypodermic needle (e.g. a crimped-on septum seal closure) whilst maintaining sterile integrity. Such containers have the additional advantage that the closure can withstand vacuum if desired (eg. to change the headspace gas or degas solutions), and withstand pressure changes such as reductions in pressure without permitting ingress of external atmospheric gases, such as oxygen or water vapour.

In an embodiment multiple dose containers comprise a single bulk vial which contains multiple patient doses, whereby single patient doses can thus be withdrawn into clinical grade syringes at various time intervals during the viable lifetime of the preparation to suit the clinical situation. Pre-filled syringes are designed to contain a single human dose, or "unit dose" and therefore may be a disposable or other syringe suitable for clinical use. The pharmaceutical compositions of the present invention may have a dosage suitable for a single patient and are provided in a suitable syringe or container, as described above.

The pharmaceutical composition may contain additional optional excipients such as: an antimicrobial preservative, pH-adjusting agent, filler, radioprotectant, solubiliser or osmolality adjusting agent. By the term "radioprotectant" is meant a compound which inhibits degradation reactions, such as redox processes, by trapping highly-reactive free radicals, such as oxygen-containing free radicals arising from the radiolysis of water. The radioprotectants of the present invention are suitably chosen from: ascorbic acid, para-aminobenzoic acid (i.e. 4-aminobenzoic acid), gentisic acid (i.e. 2,5-dihydroxybenzoic acid) and salts thereof with a biocompatible cation. By the term "biocompatible cation" ($B^c$) is meant a positively charged counterion which forms a salt with an ionised, negatively charged group, where the positively charged counterion is also non-toxic and hence suitable for administration to the mammalian body, especially the human body. Examples of suitable biocompatible cations include: the alkali metals sodium or potassium; the alkaline earth metals calcium and magnesium; and the ammonium ion. In an embodiment, biocompatible cations are sodium and potassium, more particularly sodium.

By the term "solubiliser" is meant an additive present in the composition which increases the solubility of the imaging agent in the solvent. In an embodiment, such solvent is aqueous media, and hence the solubiliser may improve solubility in water. Suitable such solubilisers include: $C_{1-4}$ alcohols; glycerine; polyethylene glycol (PEG); propylene glycol; polyoxyethylene sorbitan monooleate; sorbitan monooloeate; polysorbates; poly(oxyethylene)poly(oxypropylene)poly(oxyethylene) block copolymers (Pluronics™); cyclodextrins (e.g. alpha, beta or gamma cyclodextrin, hydroxypropyl-β-cyclodextrin or hydroxypropyl-γ-cyclodextrin) and lecithin.

By the term "antimicrobial preservative" is meant an agent which inhibits the growth of potentially harmful micro-organisms such as bacteria, yeasts or moulds. The antimicrobial preservative may also exhibit some bactericidal properties, depending on the dosage employed. The main role of the antimicrobial preservative(s) of the present invention is to inhibit the growth of any such microorganism in the pharmaceutical composition. The antimicrobial preservative may, however, also optionally be used to inhibit the growth of potentially harmful micro-organisms in one or more components of kits used to prepare the composition prior to administration. Suitable antimicrobial preservative(s) include: the parabens, i.e. methyl, ethyl, propyl or butyl paraben or mixtures thereof; benzyl alcohol; phenol; cresol; cetrimide and thiomersal. In an embodiment antimicrobial preservative(s) are the parabens.

The term "pH-adjusting agent" means a compound or mixture of compounds useful to ensure that the pH of the composition is within acceptable limits (approximately pH 4.0 to 10.5) for human or mammalian administration. Suitable such pH-adjusting agents include pharmaceutically acceptable buffers, such as tricine, phosphate or TRIS [i.e. tris(hydroxymethyl)aminomethane], and pharmaceutically acceptable bases such as sodium carbonate, sodium bicarbonate or mixtures thereof.

By the term "filler" is meant a pharmaceutically acceptable bulking agent which may facilitate material handling during production and lyophilisation. Suitable fillers include inorganic salts such as sodium chloride, and water soluble sugars or sugar alcohols such as sucrose, maltose, mannitol or trehalose.

The radiopharmaceutical compositions of the fifth aspect may be prepared under aseptic manufacture (i.e. clean room) conditions to give the desired sterile, non-pyrogenic product. In an embodiment, the key components, especially the associated reagents plus those parts of the apparatus which come into contact with the imaging agent (e.g. vials) are sterile. The components and reagents can be sterilised by methods known in the art, including: sterile filtration, terminal sterilisation using e.g. gamma-irradiation, autoclaving, dry heat or chemical treatment (e.g. with ethylene oxide). In an embodiment, some components are sterilized in advance, so that the minimum number of manipulations needs to be carried out. As a precaution, however, it is possible to include at least a sterile filtration step as the final step in the preparation of the pharmaceutical composition.

The radiopharmaceutical compositions of the present invention may be prepared by various methods:

(i) aseptic manufacture techniques in which the $^{18}$F-radiolabelling step is carried out in a clean room environment;
(ii) terminal sterilisation, in which the $^{18}$F-radiolabelling is carried out without using aseptic manufacture and then sterilised at the last step [e.g. by gamma irradiation, autoclaving dry heat or chemical treatment (e.g. with ethylene oxide)];
(iii) aseptic manufacture techniques in which the $^{18}$F-radiolabelling step is carried out using an automated synthesizer apparatus.

In a particular embodiment, method (iii) is used, and is described more fully in the sixth aspect (below).

In a sixth aspect, the present invention provides a method of preparation of the radiopharmaceutical composition of the fifth aspect, which comprises carrying out the method of preparation of the second aspect using an automated synthesizer apparatus.

Aspects of the imaging agent, precursor and composition in the sixth aspect are as described in the first, second and fourth, and fifth aspects of the present invention respectively.

By the term "automated synthesizer" is meant an automated module based on the principle of unit operations as described by Satyamurthy et al [Clin. Positr. Imag., 2(5), 233-253 (1999)]. The term 'unit operations' means that complex processes are reduced to a series of simple operations or reactions, which can be applied to a range of materials. Such automated synthesizers may be used for the method of the present invention especially when a radiopharmaceutical composition is desired. They are commercially available from a range of suppliers [Satyamurthy et al, above], including: GE Healthcare; CTI Inc; Ion Beam Applications S.A. (Chemin du Cyclotron 3, B-1348 Louvain-La-Neuve, Belgium); Raytest (Germany) and Bioscan (USA).

Commercial automated synthesizers also provide suitable containers for the liquid radioactive waste generated as a result of the radiopharmaceutical preparation. Automated synthesizers are not typically provided with radiation shielding, since they are designed to be employed in a suitably configured radioactive work cell. The radioactive work cell provides suitable radiation shielding to protect the operator from potential radiation dose, as well as ventilation to remove chemical and/or radioactive vapours. The automated synthesizer may comprise a cassette.

By the term "cassette" is meant a piece of apparatus designed to fit removably and interchangeably onto an automated synthesizer apparatus (as defined above), in such a way that mechanical movement of moving parts of the synthesizer controls the operation of the cassette from outside the cassette, i.e. externally. Suitable cassettes comprise a linear array of valves, each linked to a port where reagents or vials can be attached, by either needle puncture of an inverted septum-sealed vial, or by gas-tight, marrying joints. Each valve has a male-female joint which interfaces with a corresponding moving arm of the automated synthesizer. External rotation of the arm thus controls the opening or closing of the valve when the cassette is attached to the automated synthesizer. Additional moving parts of the automated synthesizer are designed to clip onto syringe plunger tips, and thus raise or depress syringe barrels.

The cassette is versatile, typically having several positions where reagents can be attached, and several suitable for attachment of syringe vials of reagents or chromatography cartridges (e.g. solid phase extraction or SPE). The cassette always comprises a reaction vessel. Such reaction vessels may be from 1 to 10 cm$^3$ in volume, more particularly 2 to 5 cm$^3$ in volume and are configured such that 3 or more ports of the cassette are connected thereto, to permit transfer of reagents or solvents from various ports on the cassette. In an embodiment, the cassette has 15 to 40 valves in a linear array, more particularly 20 to 30, with 25 being provided in an embodiment. The valves of the cassette may be each identical, and more particularly are 3-way valves. The cassettes are designed to be suitable for radiopharmaceutical manufacture and are therefore manufactured from materials which are of pharmaceutical grade and ideally also are resistant to radiolysis.

In an embodiment, automated synthesizers of the present invention comprise a disposable or single use cassette which comprises all the reagents, reaction vessels and apparatus necessary to carry out the preparation of a given batch of radiofluorinated radiopharmaceutical. The cassette means that the automated synthesizer has the flexibility to be capable of making a variety of different radiopharmaceuticals with minimal risk of cross-contamination, by simply changing the cassette. The cassette approach also has the advantages of: simplified set-up hence reduced risk of operator error; improved GMP (Good Manufacturing Practice) compliance; multi-tracer capability; rapid change between production runs; pre-run automated diagnostic checking of the cassette and reagents; automated barcode cross-check of chemical reagents vs the synthesis to be carried out; reagent traceability; single-use and hence no risk of cross-contamination, tamper and abuse resistance.

Included in an aspect of the invention, is the use of an automated synthesizer apparatus to prepare the radiopharmaceutical composition of the second aspect.

Included in an aspect of the invention, is the use of a suitable cassette in conjunction with an automated synthesizer apparatus to prepare the radiopharmaceutical composition of the second aspect.

In the sixth aspect, the precursor is provided in sterile, lyophilized form. The lyophilized precursor may be provided as a non-radioactive kit in a pharmaceutical grade container, for example, a septum-sealed vial, as is described in the fifth aspect (above).

Aspects of the imaging agent or composition in the sixth aspect are as described in the first and fifth aspects respectively of the present invention (above).

In a seventh aspect, the present invention provides a method of imaging the human or animal body which comprises generating an image of at least a part of the body to which the imaging agent of the first aspect, or the composition of the fifth aspect has distributed using PET, wherein the imaging agent or composition has been previously administered to the body.

Aspects of the imaging agent or composition in the seventh aspect are as described in the first and fifth aspects respectively of the present invention (above).

Also included in embodiments of the invention is a method of diagnosis of the human or animal body which comprises the imaging method of the sixth aspect.

Embodiments of the invention is illustrated by the non-limiting Examples detailed below. All reactions were operated under a nitrogen atmosphere with standard Schlenk glassware, vacuum or glove box techniques unless otherwise noted. The solvents were dried and degassed by refluxing over standard drying agents and distilled immediately prior to use.

Example 1 provides the synthesis of an amide-functionalised tacn chelator of the invention having 3 pendant amide functional groups (Chelator 3). Examples 2 and 3 provide the preparation of gallium trichloro and trifluoro complexes respectively of Chelator 3. Such gallium complexes are suitable as non-radioactive precursor metal complexes for $^{18}F$-radiolabelling. Example 4 provides a prophetic Example of the synthesis of a tacn chelator having a single pendant amide functional group. Example 5 shows that the Ga(III) ligand exchange and fluoride incorporation proceed successfully using Ga(NO$_3$)$_3$, when the system is buffered to pH 4.

Example 6 and FIG. 1 provide supporting evidence for the hydrogen bonding interaction of the present invention—in particular for the occurrence of significant H-bonding between the [GaF$_3$(R$_3$-tacn)] units and [NH$_4$]$^+$, or H$_2$O (as well as F•••M interactions where M=Na$^+$ or K$^+$).

TABLE 1

Chelators of the Invention.

| Chelator | R$^b$ |
|---|---|
| Chelator 1 | H |
| Chelator 2 | CH$_3$ |
| Chelator 3 | phenyl |

Chelator 1 nd Chelator 2 are described in the literature [Weyhermuller et al, JCS., Dalton Trans., 3805-3814 (1998)]. Chelator 1 is also described by Zhang et al [Inorg. Chem. Commun., 269-272 (2006)] and Amin et al [Inorg. Chim. Acta, 246, 99-107 (1996)]. The synthesis of Chelator 3 is provided in Example 1.

Abbreviations

Boc: tert-Butyloxycarbonyl.
Bz: benzyl;
DMF: dimethylformamide
DMSO: Dimethylsulfoxide.
GMP: Good Manufacturing Practice.
HPLC: High performance liquid chromatography.
Me: methyl.
MeCN: acetonitrile.
SPE: solid phase extraction.
Tacn: 1,4,7-triazacyclononane
THF: tetrahydrofuran.
tBu: tert-Butyl.

Example 1

Preparation of N,N',N''-tris(-N-phenyl(methylcarboxamide))-1,4,7-triazacyclononane (Chelator 3)

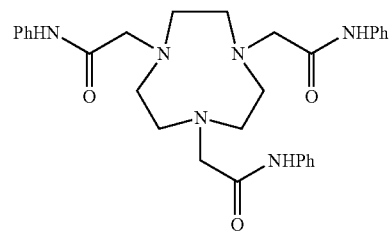

Step (i): 2-Chloro-N-phenyl acetamide.

A solution of aniline (18.3 mL, 0.20 mol) in acetone was cooled to 0.0 in an ice bath. Chloroacetyl chloride (8.2 mL, 0.10 mol) was added dropwise via a syringe under a dry N$_2$ atmosphere. The addition resulted in the formation of a brown precipitate. The mixture was stirred at room temperature for 4 h. and was then treated with 40 mL 10% HCl solution. This dissolved the brown precipitate, and caused the formation of a white solid. The solid was isolated by filtration and washed with 40 mL 10% HCl and 80 mL H$_2$O. The white crystalline solid was dried under high vacuum for 6 h. Yield 16.32 g, 96%.

$^1$H NMR (300 MHz, CDCl$_3$, 298 K): δ 4.19 (s [2H] COCH$_2$Cl), 7.18 (tt [1H] ArCH), 7.37 (tt [2H] ArCH), 7.55 (dt [2H] ArCH), 8.29 (br s [1H] N—H) ppm. $^{13}$C {1H} NMR (CDCl$_3$, 298 K): δ 42.85 (COCH$_2$Cl), 120 (ArCH), 125 (ArCH), 129 (ArCH), 137 (ArCH), 164 (CO) ppm.

Step (ii): N,N',N''-tris(-N-phenyl(methylcarboxamide)-1,4,7-triazacyclononane.

To a rapidly stirring mixture of K$_2$CO$_3$ (5.0 g, 12 mmol) in 40 mL acetone at 45° C. was added H$_3$-tacn (0.50 g, 3.87 mmol). The mixture was stirred for 10 mins. at 45° C. A solution of 2-chloro-N-phenylacetamide (1.97 g, 11.6 mmol) in 20 ml acetone was added dropwise. The resultant mixture was heated at 45° C. for 24 h. The mixture was filtered and the resulting pale yellow solution was concentrated under high vacuum. The pale yellow solid which was washed with MeCN and hexane to give Chelator 3 as a white crystalline solid. Yield 1.33 g, 71%. ESI+MS (MeOH): m/z 529.2 (100%) [M+H+]. +]. IR (Nujol) ν 3315, 3188, 1683, 1599, 503, 353 cm$^{-1}$. $^1$H NMR (300 MHz, CD$_3$OD, 298 K): δ 3.17 (s [12H] tacn CH$_2$), 3.90 (s [6H] N—CH$_2$CO$_2$), 7.01-6.98 (m [9H] ArCH), 7.50-7.48 (m [6H] ArCH) ppm. $^{13}$C NMR (CD$_3$OD, 298 K): δ 50.8 (tacn CH$_2$), 59.2 (N—CH$_2$CO), 121.2, 125.1, 129.6, 139.1 (Ar CH), 163.9 (CO) ppm. Recrystallization from hot MeCN and Et$_2$O yielded colourless crystals suitable for single crystal X-ray diffraction.

Example 2

Preparation of the Gallium Trichloride Complex of Chelator 3 [GaCl$_3$((CH$_2$CONHPh)$_3$-tacn)]

A solution of Chelator 3 (Example 1; 0.075 g, 0.15 mmol) in anhydrous CH$_2$Cl$_2$ (6 mL) was added dropwise to a solution of GaCl$_3$ (0.025 g, 0.15 mmol) in anhydrous CH$_2$Cl$_2$ (5 mL). A white precipitate was formed instantly. The mixture was stirred at room temperature for 4 h. The solid was isolated by filtration and washed with 4×5 mL CH$_2$Cl$_2$ and 5 mL hexane. The solid was dried under high vacuum for 6 h. White solid. Yield 0.082 g, 77%. IR (Nujol): ν 3267, 3200, 1695, 376, 369 cm$^{-1}$.

$^1$H NMR (300 MHz, CD$_3$CN, 298 K): δ 3.06 (br m [12H] tacn CH$_2$), 3.78 (s [6H] N—CH$_2$—CO), 7.10 (m [6H] ArCH), 7.35 (m [3H] ArCH), 7.50 (m [6H] Ar CH). 8.73 (br s [3H] N—H) ppm.

Example 3

Preparation of the Gallium Trifluoride Complex of Chelator 3 [GaF$_3$((CH$_2$CONHPh)$_3$-tacn)]

To a fine suspension of [GaCl$_3$((CH$_2$CONHPh)$_3$-tacn)] (Example 2; 0.018 g, 0.026 mmol) in anhydrous MeCN was added KF (0.005 g, 0.079 mmol) in water (2 mL). Addition of the KF resulted in the dissolution of the precursor compound. The mixture was stirred at room temperature for 15 h. A very fine white precipitate formed (KCl). This was removed by filtration and the filtrate concentrated under high vacuum to give a white solid. This was washed with hexane and dried under high vacuum. White solid. Yield: ~70%. IR (Nujol): ν 3331, 1695, 504, 467 cm$^{-1}$.

$^1$H NMR (300 MHz, D$_2$O, 298 K) δ 3.23-3.12 (br m [12H] tacn CH$_2$), 3.89 (s [6H] N—CH$_2$—CO), 7.21-7.13 (m [6H] ArCH), 7.30-7.27 (m [3H] ArCH), 7.45-7.43 (m [6H] ArCH). 9.09 (br s [3H] N—H) ppm. $^{19}$F{$^1$H} NMR (D$_2$O, 298 K) δ −176.3 (br s) ppm.

Example 4

Synthesis of 1-(N-phenyl(methylcarboxamide))-4,7-diisopropyl-1,4,7-triazacyclononane (Prophetic Example)

To a rapidly stirring mixture of K$_2$CO$_3$ in acetone at 45° C. is added 1,4-diisopropyl-1,4,7-triazacyclononane [HiPr$_2$-tacn; synthesised by the literature method of Mahapatra et al, J. Org. Chem., 47, 412 (1982)]. After stirring for 10 mins. at 45° C., a solution of 2-chloro-N-phenyl acetamide (1 mol. equiv.) in 20 mL acetone is added dropwise. The resultant mixture is heated at 45° C. for 24 h. The mixture is then filtered and the resulting pale yellow solution concentrated under high vacuum.

Example 5

Synthesis of Representative Gallium Complexes from Ga(III) Nitrate Starting Material Ga(NO$_3$)$_3$.9H$_2$O (Sigma-Aldrich) was dissolved in pH 4 buffered NaOAc in H$_2$O/D$_2$O. A signal (δ=0) was observed in the $^{71}$Ga NMR spectrum ([Ga(H$_2$O)$_6$]$^{3+}$). Addition of one equivalent of Me$_3$-tacn gave a slightly turbid solution. The $^{71}$Ga NMR spectrum of this mixture indicated the loss of the resonance at δ=0, with no new resonance observed.

Three molar equivalents of KF (in buffer) were then added and the mixture stirred for 30 minutes at room temperature. This led to the appearance of a resonance in the $^{71}$Ga NMR spectrum which matched that for the complex [GaF$_3$(Me$_3$-tacn)] (δ=45 ppm). $^1$H and $^{19}$F{$^1$H} NMR spectroscopy of the concentrated reaction solution matched those observed for the trifluoride complex, as detailed by Bhalla et al [Chem. Sci., 5, 381-391 (2014)], further confirming that the reaction had proceeded.

Example 6

Evidence for F•••H and F•••M Bonding between [GaF$_3$(R$_3$-tacn)] with [NH$_4$]$^+$, Na$^+$, K$^+$ ESI+ mass spectrometry of [GaF$_3$(BzMe$_2$-tacn)] [see Bhalla et al Chem. Sci., 5, 381-391 (2014), doi:10.1039/C3SC52104D], indicated the presence of [GaF$_3$(BzMe$_2$-tacn)+NH$_4$]$^+$ in solution (NH$_4$OAc). Specifically, the highly electronegative MF$_3$ unit interacted with ammonium cations in the mobile phase to create a species of the form {[GaF$_3$L]$^+$ NH$_4$}$^+$ which was detected by ESI+MS.

A number of related ESI MS experiments were performed using the model compound [GaF$_3$(Me$_3$-tacn)].4H$_2$O with a variety of cations, ranging from Group I cations and the organic cations (ammonium and imidazolium) (M$^+$). These experiments also provided evidence (m/z and isotopic distributions) for formation of [GaF$_3$(Me$_3$-tacn)+M]$^+$ in each case.

In addition to this, a number of common salts (NaBF$_4$, KPF$_6$, NH$_4$PF$_6$) were added to the complexes [MF$_3$L] L=Me$_3$-tacn and BzMe$_2$-tacn in aqueous solution. The solutions were allowed to slowly evaporate in air. This led to crystallisation of 3 different species, [GaF$_3$(BzMe$_2$-tacn)+Na][BF$_4$], [GaF$_3$(BzMe$_2$-tacn)+K][PF$_6$] and [GaF$_3$(BzMe$_2$-tacn)+Na+NH$_4$][PF$_6$]$_2$, each revealing significant F•••H or F•••M interactions. See FIG. 1.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An imaging agent which comprises an $^{18}$F-labelled compound of Formula I:

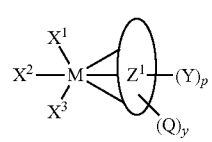

(I)

where:
X$^1$, X$^2$ and X$^3$ are independently $^{19}$F or $^{18}$F, with the proviso that at least one of X$^1$, X$^2$ and X$^3$ is $^{18}$F;
M is Ga$^{3+}$ or In$^{3+}$;
Z$^1$ is a tridentate triamine chelating agent wherein all 3 amine donors are bound to M, wherein
Z$^1$ has at least one Y group, and optionally also a Q group covalently conjugated thereto;
p is 1, 2 or 3;
y is 0 or 1;

where $Z^1$ is of Formula $Z^a$:

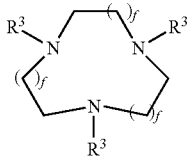

where each $R^3$ is independently H, $C_{1-4}$ alkyl, $C_{2-4}$ alkoxyalkyl, $C_{1-4}$ hydroxyalkyl, a Y group or a Q group;
each f is independently 1 or 2;
or Formula $Z^{aa}$ or Formula $Z^{ab}$:

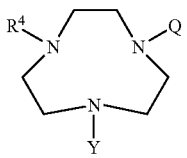

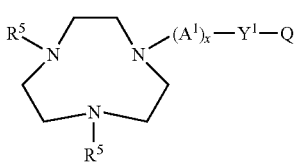

where $R^4$ is H, $C_{1-4}$ alkyl, $C_{2-4}$ alkoxyalkyl, $C_{1-4}$ hydroxyalkyl or a Y group;
$R^5$ is H, $C_{1-4}$ alkyl, $C_{2-4}$ alkoxyalkyl or $C_{1-4}$ hydroxyalkyl;
Y is independently $-(A^1)_x-Y^1$ or $-(A^1)_x-Y^1-Q$ where each $A^1$ is independently $-CH_2-$ or $-O-$;
wherein x is an integer of value 1 to 6; and
$Y^1$ is $-NHR^a$, $-NH(CH_2)_2NHR^a$, $-NH(CH_2)_3NHR^a$, $-(C=O)NHR^a$, $-NH(C=O)R^a$, $-NH(C=NH)NHR^a$, $-OR^a$, $R^a$, a $Y^2$ group or a $Y^3$ group;
$Y^2$ is:

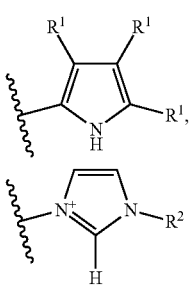 or 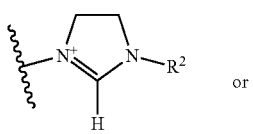

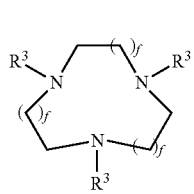

$Y^3$ is Arg, Lys, Asn, Gln, Ser, Thr or Tyr;
wherein $R^a$ is independently H, $C_{1-4}$ alkyl, $C_{2-4}$ alkenyl, $C_{2-4}$ alkynyl, $C_{2-4}$ alkoxyalkyl, $C_{1-4}$ hydroxyalkyl, or -phenyl;
and wherein each $R^1$ is independently $C_{1-4}$ alkyl, $C_{2-4}$ alkoxyalkyl or $C_{1-4}$ hydroxyalkyl;
and $R^2$ is independently H, $C_{1-4}$ alkyl or $Si(C_{1-4}$ alkyl$)_3$;
Q is -L-[BTM];
L is a synthetic linker group of formula $-(A)_m-$ wherein each A is independently $-CR_2-$, $-CR=CR-$, $-C\equiv C-$, $-CO_2CR_2-$, $-NRCO-$, $-CONR-$, $-CR=N-O-$, $-NR(C=O)NR-$, $-NR(C=S)NR-$, $-SO_2NR-$, $-NRSO_2-$, $-CR_2OCR_2-$, $-CR_2SCR_2-$, $-CR_2NRCR_2-$, a $C_{4-8}$ cycloheteroalkylene group, a $C_{4-8}$ cycloalkylene group, $-Ar-$, $-NR-Ar-$, $-O-Ar-$, $-Ar-(CO)-$, an amino acid, a sugar or a monodisperse polyethyleneglycol (PEG) building block, wherein each R is independently chosen from H, $C_{1-4}$ alkyl, $C_{2-4}$ alkenyl, $C_{2-4}$ alkynyl, $C_{2-4}$ alkoxyalkyl or $C_{1-4}$ hydroxyalkyl;

m is an integer of value 1 to 20;

each Ar is independently a $C_{5-12}$ arylene group, or a $C_{3-12}$ heteroarylene group;

BTM is a biological targeting moiety.

2. The imaging agent of claim 1, where one Q group is present.

3. The imaging agent of claim 1, where each Y group is covalently conjugated to a different amine donor atom of $Z^1$.

4. The imaging agent of claim 1, where the biological targeting moiety is chosen from: a single amino acid, a 3-100 mer peptide, an enzyme substrate, an enzyme antagonist, an enzyme agonist, an enzyme inhibitor or a receptor-binding compound.

5. A method of preparation of the imaging agent which comprises an $^{18}F$-labelled compound of Formula I:

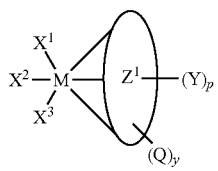

(I)

where:
$X^1$, $X^2$ and $X^3$ are independently Br, Cl, $^{19}F$ or $^{18}F$, with the proviso that at least one of $X^1$, $X^2$ and $X^3$ is $^{18}F$;

M is $Ga^{3+}$ or $In^{3+}$;

$Z^1$ is a tridentate triamine chelating agent wherein all 3 amine donors are bound to M, wherein $Z^1$ has at least one Y group, and optionally also a Q group covalently conjugated thereto;

p is 1, 2 or 3;

y is 0 or 1;

where $Z^1$ is of Formula $Z^a$:

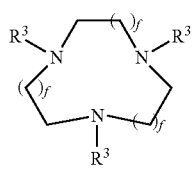

where each $R^3$ is independently H, $C_{1-4}$ alkyl, $C_{2-4}$ alkoxyalkyl, $C_{1-4}$ hydroxyalkyl, a Y group or a Q group;
each f is independently 1 or 2;

or Formula $Z^{aa}$ or Formula $Z^{ab}$:

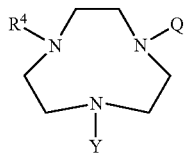
($Z^{aa}$)

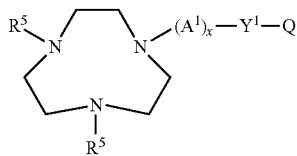
($Z^{ab}$)

where $R^4$ is H, $C_{1-4}$ alkyl, $C_{2-4}$ alkoxyalkyl, $C_{1-4}$ hydroxyalkyl or a Y group;
$R^5$ is H, $C_{1-4}$ alkyl, $C_{2-4}$ alkoxyalkyl or $C_{1-4}$ hydroxyalkyl;
Y is independently -$(A^1)_x$-$Y^1$ or -$(A^1)_x$-$Y^1$-Q where each $A^1$ is independently —$CH_2$— or —O—;
wherein x is an integer of value 1 to 6; and
$Y^1$ is —$NHR^a$, —$NH(CH_2)_2NHR^a$, —$NH(CH_2)_3NHR^a$, —(C=O)$NHR^a$, —NH(C=O)$R^a$, —NH(C=NH)$NHR^a$, —$OR^a$, $R^a$, a $Y^2$ group or a $Y^3$ group;
$Y^2$ is:

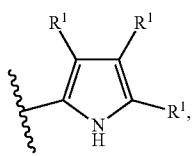 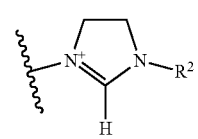 or

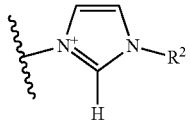

$Y^3$ is Arg, Lys, Asn, Gln, Ser, Thr or Tyr;
wherein $R^a$ is independently H, $C_{1-4}$ alkyl, $C_{2-4}$ alkenyl, $C_{2-4}$ alkynyl, $C_{2-4}$ alkoxyalkyl, $C_{1-4}$ hydroxyalkyl, or -phenyl;
and wherein each $R^1$ is independently $C_{1-4}$ alkyl, $C_{2-4}$ alkoxyalkyl or $C_{1-4}$ hydroxyalkyl;
and $R^2$ is independently H, $C_{1-4}$ alkyl or Si$(C_{1-4}$ alkyl$)_3$;
Q is -L-[BTM];
L is a synthetic linker group of formula -$(A)_m$- wherein each A is independently —$CR_2$—, —CR=CR—, —C≡C—, —$CO_2CR_2$—, —NRCO—, —CONR—, —CR=N—O—, —NR(C=O)NR—, —NR(C=S)NR—, —$SO_2NR$—, —$NRSO_2$—, —$CR_2OCR_2$—, —$CR_2SCR_2$—, —$CR_2NRCR_2$—, a $C_{4-8}$ cycloheteroalkylene group, a $C_{4-8}$ cycloalkylene group, —Ar—, —NR—Ar—, —O—Ar—,
—Ar—(CO)—, an amino acid, a sugar or a monodisperse polyethyleneglycol (PEG) building block, wherein each R is independently chosen from H, $C_{1-4}$ alkyl, $C_{2-4}$ alkenyl, $C_{2-4}$ alkynyl, $C_{2-4}$ alkoxyalkyl or $C_{1-4}$ hydroxyalkyl;
m is an integer of value 1 to 20;
each Ar is independently a $C_{5-12}$ arylene group, or a $C_{3-12}$ heteroarylene group;
BTM is a biological targeting moiety,
the method comprising, reacting a precursor with a supply of [$^{18}$F]-fluoride or [$^{18}$F]NaF, optionally in the presence of [$^{19}$F]-fluoride, in a suitable solvent to form the compound of Formula I,
wherein said precursor comprises a metal complex of a chelator of Formula II:

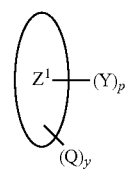
(II)

where $Z^1$, Y, Q, p and q are as defined in Formula I;
and where said metal is chosen from: $Ga^{3+}$ or $In^{3+}$.

6. The method of claim 5, where said precursor is of Formula III:

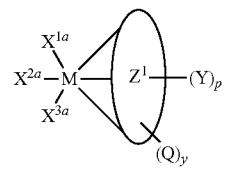
(III)

where $X^{1a}$, $X^{2a}$ and $X^{3a}$ are independently Br or Cl.

7. The method of claim 6, where $X^{1a}$=$X^{2a}$=$X^{3a}$=Cl.

8. A radiopharmaceutical composition which comprises the imaging agent of claim 1, together with a biocompatible carrier, in a form suitable for mammalian administration.

* * * * *